United States Patent [19]

Zare et al.

[11] Patent Number: 5,232,565
[45] Date of Patent: Aug. 3, 1993

[54] CAPILLARY ELECTROPHORETIC SYSTEM

[75] Inventors: Richard N. Zare, Stanford; Stephen L. Pentoney, Jr.; John W. Frost, both of Menlo Park; Jeff Quint, Orange, all of Calif.

[73] Assignee: The Board of Trustees of the Leland Stanford Junior University, Stanford, Calif.

[21] Appl. No.: 873,714

[22] Filed: Apr. 22, 1992

Related U.S. Application Data

[60] Continuation of Ser. No. 447,270, Dec. 7, 1989, abandoned, which is a division of Ser. No. 249,999, Sep. 27, 1988, abandoned.

[51] Int. Cl.$^5$ .................. G01N 27/26; G01N 27/447
[52] U.S. Cl. ............................. 204/180.1; 204/299 R
[58] Field of Search ..................... 204/180.1, 299 R

[56] References Cited

U.S. PATENT DOCUMENTS

| | | | |
|---|---|---|---|
| 3,948,753 | 4/1976 | Arlinger | 204/299 R |
| 4,154,669 | 5/1979 | Goetz | 204/299 R |
| 4,175,662 | 11/1979 | Zold | 209/552 |
| 4,394,263 | 7/1983 | Dosch et al. | 210/198.2 |
| 4,459,198 | 8/1984 | Mizumo et al. | 204/299 R |
| 4,529,230 | 7/1985 | Fatula, Jr. | 285/341 |
| 4,675,300 | 6/1987 | Zare et al. | 436/174 |
| 4,680,201 | 7/1987 | Hjerten | 427/230 |
| 4,830,830 | 5/1989 | Tamotu et al. | 204/299 R X |
| 4,909,919 | 3/1990 | Morris et al. | 204/180.1 |
| 5,045,172 | 9/1991 | Guzman | 204/299 R |

FOREIGN PATENT DOCUMENTS

| | | |
|---|---|---|
| 0070963 | 3/1982 | European Pat. Off. . |
| 070963 | 3/1982 | European Pat. Off. . |
| 0271440 | 11/1987 | European Pat. Off. . |
| 271440 | 11/1987 | European Pat. Off. . |
| 3620235 | 12/1986 | Fed. Rep. of Germany . |
| 3620235 | 12/1986 | Fed. Rep. of Germany . |
| 53-29193 | 3/1978 | Japan . |
| 58-148951 | 9/1983 | Japan . |
| 60-138447 | 7/1985 | Japan . |
| 60-138450 | 7/1985 | Japan . |
| 60-140151 | 7/1985 | Japan . |

OTHER PUBLICATIONS

"On-Line Radioisotope Detection for Capillary Electrophoresis," by Pentoney et al, *Analytical Chemistry*, vol. 61, No. 15, pp. 1642-1647, Washington, D.C. Aug. 1, 1989.

Verheggen et al., "Simple Sampling Device for Capillary . . . ," Journ. of Chromatography, 452:615-622 (1988).

(List continued on next page.)

*Primary Examiner*—Donald R. Valentine
*Assistant Examiner*—John S. Starsiak, Jr.
*Attorney, Agent, or Firm*—Majestic, Parsons, Siebert & Hsue

[57] ABSTRACT

In the capillary electrophoretic system, the components of a sample to be separated and detected are labelled by a radioactive material which emits gamma rays or beta particles with energy high enough to penetrate the electrolyte and the capillary tube. A semiconductor detector outside the tube and placed adjacent to the tube detects the gamma rays or beta particles in order to detect the presence of the components of the sample. A weaker radio-label may also be used in conjunction with scintillating material which is introduced together with the sample into the tube or through a different tube. Alternatively, the scintillating material may be placed inside the tube or made a part of the tube. The scintillating material emits light in response to radiation from the radio labels on the components of the sample to enable detection of the component. The power supply for driving the electrolyte in the tube is controlled by a control system in response to the detector signal to reduce the voltage, turn the power supply off or apply a voltage of opposite polarity in order to increase the residence time of a particular component which has been detected or to make it pass the detector region two or more times. By increasing the residence time, the sensitivity of detection is increased.

19 Claims, 3 Drawing Sheets

OTHER PUBLICATIONS

Deml et al., "Electric Sample Splitter for . . . ," *Journal of Chromatography*, 320:159–165 (1985).

Miyaguchi et al., "Microbore High-Preformance Liquid Chromatography . . . ," Journal of Chromatography, 316:501–505 (1984).

Watanabe, "Amperometric Detection of Muramic Acid in High-Performance . . . ," Journal of Chromatography, 316:495–500 (1984).

Arlinger, "Preparative Capillary Isotachophoresis, Principle . . . ," Journal of Chromatography, 119:9–24 (1976).

Lillig et al., "Fundamentals of Reaction Detection Systems," *Reaction Detection in Liquid Chromatography*, pp. 1–15.

"On-Line Radioisotope Detection for Capillary . . . ," by Pentoney et al., Anal. Chem., vol. 61, No. 15, pp. 1642–1647, Washington D.C. Aug. 1, 1989.

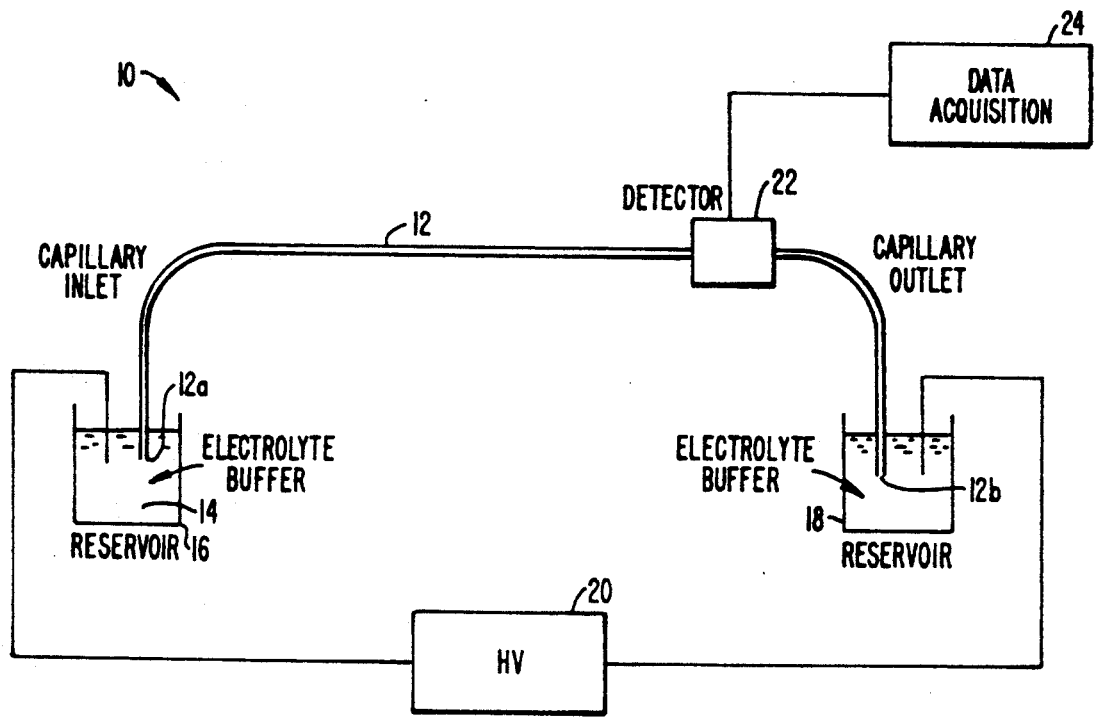
FIG._1.
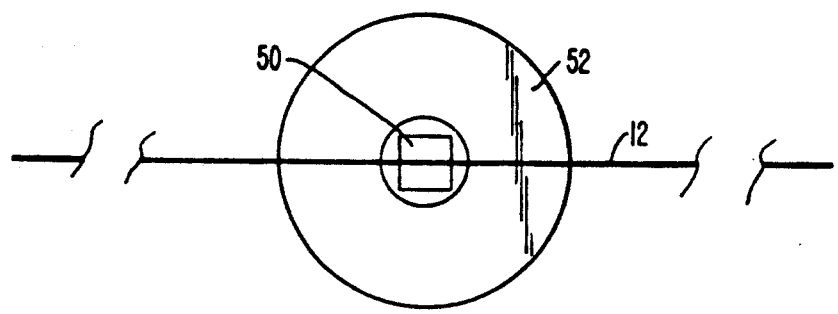
FIG._2.

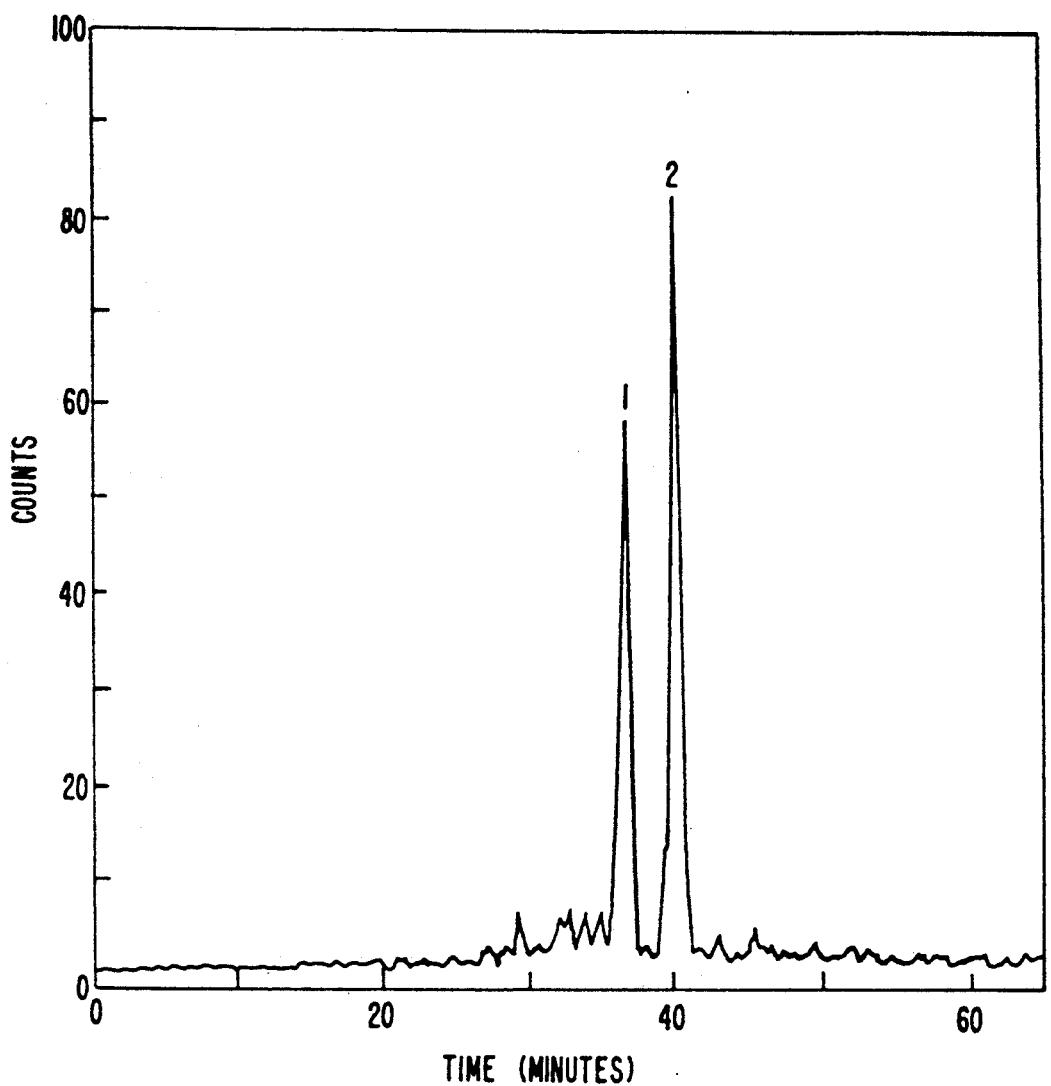
FIG._3.
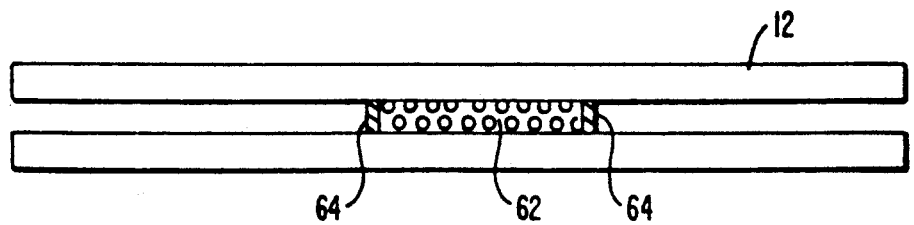
FIG._4A.

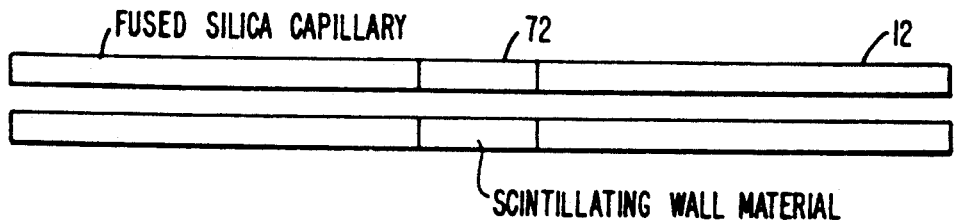
FIG._4B.
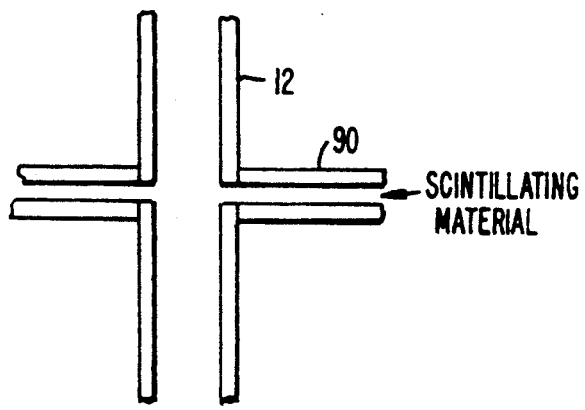
FIG._5.
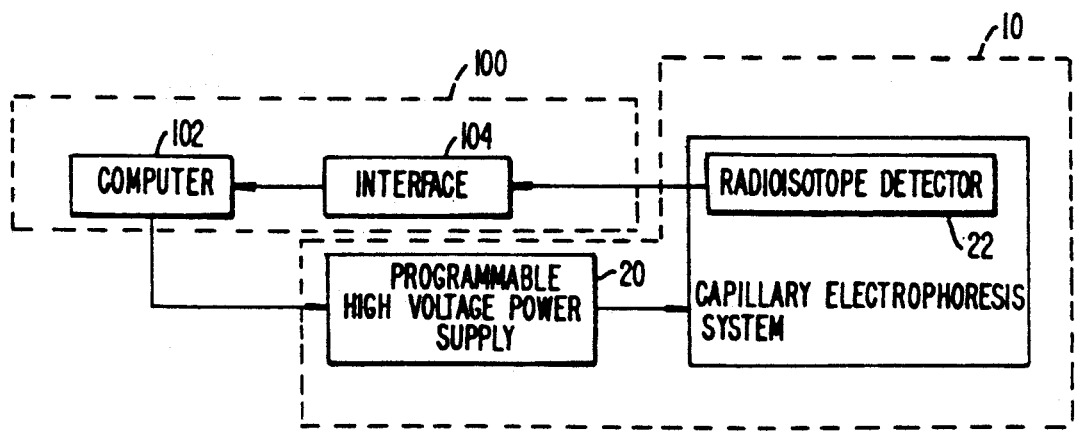
FIG._6.

CAPILLARY ELECTROPHORETIC SYSTEM

This is a continuation of application Ser. No. 447,270, filed Dec. 7, 1989, now abandoned, which is a divisional of Ser. No. 07/249,999, filed Sep. 27, 1988, now abandoned.

BACKGROUND OF THE INVENTION

This invention relates in general to capillary electrophoretic systems and in particular to an improved capillary zone electrophoretic system for detection of substances.

Capillary zone electrophoresis (CZE) in small capillaries has proven useful as an efficient method for the separation of solutes. An electric field is applied between the two ends of a capillary tube into which an electrolyte containing the solutes is introduced. The electric field causes the electrolyte to flow through the tube. Some solutes will have higher electrokinetic mobilities than other solutes so that the sample components are resolved into zones in the capillary tube during the flow of the electrolytes through the capillary.

CZE is advantageous since it requires only very small sample volumes such as the contents of a cell or cellular subcompartments. For these and other reasons, CZE has shown great promise as a separation and detection technique.

One of the major challenges in CZE is to improve selectivity and sensitivity of detection. To improve selectivity of detection, it is desirable to employ detectors which respond only to certain sample components but not to others; this permits detection of the origin of certain sample components despite chemical changes and the presence of other components and substances. Since the amounts of materials used in CZE are so minute, detectors used must have high sensitivity. One way to increase detection selectivity and detection sensitivity is to use radio-labels. In "Presentations on High Performance Electrophoresis at the 1988 Pittsburgh Conference", LC.GC, Vol. 6, No. 6, pp. 484–491 at 488, a radioactive detection technique designed for capillary electrophoresis is described for detecting pharmaceuticals labelled by a radio-label containing technetium, a gamma emitter with a six hour half life. A capillary tube containing the radio-labelled pharmaceutical is passed through a hole drilled in a scintillation crystal. The latter emits light when gamma rays strike it. By passing the sample through a capillary tube enclosed by a scintillation crystal, activation of the scintillation crystal by radiation is permitted from all sides of the capillary. This technique was presented in the 1988 Pittsburg conference by Altria, Simpson, Bharij and Theobald.

The above-described method is not entirely satisfactory. It is therefore desirable to provide an improved electrophoretic system employing radioactive detection.

In conventional capillary zone electrophoresis, the time period during which a detector can be used for detecting a substance is constrained by the speed of movement of the sample zone through the capillary. Consequently, the detection of minute quantities of substances may be difficult. It is therefore desirable to provide an improved capillary zone electrophoretic system in which such difficulty is alleviated.

SUMMARY OF THE INVENTION

One aspect of the invention is directed towards an electrophoretic apparatus for detecting the presence of a substance in a sample introduced into an electrolyte in a capillary tube having two ends. The apparatus comprises means for applying a voltage to the capillary tube to move the electrolyte from one end of the tube to the other for separating the sample into its component; and a radioactive material which is attached to or incorporated into the substance. The radioactive material emits gamma rays or beta particles with energy high enough to penetrate the medium and the tube. The apparatus further comprises a semiconductor detector outside the tube and placed adjacent to the tube for detecting the gamma rays or beta particles emitted by the radioactive material in order to detect the presence of the substance.

Another aspect of the invention is directed towards an electrophoretic apparatus for detecting the presence of a substance in a sample introduced into an electrolyte in a capillary tube having two ends where the tube contains an electrolyte. The apparatus comprises means for applying a voltage to the capillary tube to move the electrolyte from one end of the tube to the other for separating the sample into its components and a radioactive material which is attached to or incorporated in the substance. The material emits alpha, beta or gamma particles. The apparatus also comprises a scintillating material inside the tube or incorporated as part of the tube which emits electromagnetic radiation in response to alpha, beta or gamma particles; and a photodetector outside the tube for detecting the electromagnetic radiation emitted by the scintillating material in order to detect the presence of the substance.

Yet another aspect of the invention is directed towards an electrophoretic apparatus for detecting the presence in the sample introduced into an electrolyte in a capillary tube having two ends. The apparatus comprises means for applying a voltage to the capillary tube to move the electrolyte from one end of the tube to the other for separating the sample into its components; and a detector for detecting the presence of the substance. The detector provides a signal when said substance is detected by the detector. The apparatus also comprises means responsive to the signal for adjusting the voltage applied by the voltage applying means to decrease the speed of movement of the sample in the tube to increase sensitivity of detection.

BRIEF DESCRIPTION OF THE DRAWINGS

FIG. 1 is a block diagram of a capillary electrophoretic system to illustrate the invention.

FIG. 2 is a diagram showing in more detail a portion of the capillary tube and one implementation of the detector of FIG. 1 to illustrate a first embodiment of the invention.

FIG. 3 is a capillary electropherogram of quanosine $5'[\alpha\text{-}^{32}P]$ triphosphate (peak 1) and adenosine $5'[\alpha\text{-}^{32}P]$ triphosphate (peak 2), to illustrate the invention.

FIG. 4A is a diagram of a portion of the capillary tube of FIG. 1 provided with frits and scintillating beads to illustrate a second embodiment of the invention.

FIG. 4B is a diagram of a portion of the capillary tube of FIG. 1 where a portion of the tube is made of a scintillating wall material to illustrate a third embodiment of the invention.

FIG. 5 is a diagram of a capillary tube connected to a second tube to permit a flowing stream of scintillating material to be introduced into the capillary tube from the second tube.

FIG. 6 is a block diagram of a capillary electrophoretic system and a feedback control system for controlling the movement of a sample in the capillary electrophoretic system to illustrate the invention.

DETAILED DESCRIPTION OF THE INVENTION

FIG. 1 is a block diagram of an electrophoretic system 10 to illustrate the invention. As shown in FIG. 1, apparatus 10 includes a capillary tube 12 with an inlet end 12a and an outlet end 12b. An electrolyte buffer 14 is supplied to the tube to end 12a from a reservoir 16. The electrolyte buffer which exits from outlet end 12b is collected in reservoir 18. A high voltage is applied between the two reservoirs, causing the electrolyte to move from reservoir 16 through inlet end 12a, capillary tube 12, and end 12b into reservoir 18. The high voltage is applied by a power supply 20. As is known in conventional capillary electrophoresis, a sample is introduced into the inlet end 12a, such as by dipping end 12a for a short time into a sample and applying a voltage across the tube to move a small portion of the sample into the tube. The end 12a is then dipped into reservoir 16, where the portion of the sample is then carried under the influence of the electric field through tube 12 towards end 12b. As is also known in the electrophoretic art, different components of the sample may move with different speeds in tube 12, causing the components to separate along the length of the tube. These components are detected by detector 22 when the components pass the detector. Signals from detector 22 are sent to a data acquisition system 24 for analysis and recording.

As described earlier in the background of the invention, one of the problems in capillary zone electrophoresis is the lack of sensitivity of detection since the components of the sample may be present only in very small amounts. The technique presented by Altria in the 1988 Pittsburgh conference discussed above is apparently an attempt to increase the sensitivity of detection by employing radioactive detection. While such technique may increase detection sensitivity, the technique is disadvantageous because it is not compact; it requires shielding and it involves costly scintillation detectors.

The above described difficulties with the technique presented by Altria et al. is overcome in this invention by employing a detector which is capable of detecting the radioactive emission by a radioactive material in the sample to be analyzed directly without requiring any scintillating material or scintillation detectors.

FIG. 2 is a diagram illustrating in more detail one implementation of detector 22 which detects directly the radioactive emission from components in the sample introduced in tube 12 of FIG. 1. As shown in FIG. 2, the detector may comprise a cadmium telluride (CdTe) wafer 50 mounted in an aluminum housing 52. In reference to FIG. 1, a sample containing a component which has been radio-labeled is injected into end 12a of tube 12. When the component passes detector 22, the radioactive emission from the component is detected by the CdTe wafer, which generates a signal which is supplied to data acquisition block 24 to indicate the presence of such component. A suitable radio-label may include the isotope $^{32}P$, or the isotope $^{125}I$. It will be understood that other types of radioactive elements or substances may be used as long as the radioactive emission from such material is strong enough to penetrate the electrolyte buffer 14 in the tube and the wall of tube 12. Any such radioactive material may be used and are within the scope of the invention. Since the radioactive emission of the radio-label must be capable of penetrating the electrolyte buffer as well as the tube wall, the present state of the technology may limit the radio-labels used to gamma ray emitters and hard beta ray emitters. Semiconductors other than CdTe in the form of wafers or other forms may also be used. Examples are silicon and germanium.

As is known in the art, samples with components which are radio-labelled may be prepared using radio-labeled chemicals as the starting material. Such chemicals are available from, for example, Amersham Corporation in Arlington Heights, Ill. or ICN Biomedicals, Inc. in Costa Mesa, Calif.

In the detection scheme described by Altria et al. above, scintillation crystal and optical detectors are required. The embodiment described above in reference to FIG. 2, the gamma or beta rays are detected directly by a detector without requiring the use of scintillation crystals or optical detectors and is therefore much simpler than Altria et al.'s scheme Furthermore, the semiconductor detector of FIG. 2 is compact and easy to use. Such embodiment of the invention is therefore advantageous over the device of Altria et al.

In the embodiment described above in reference to FIG. 2, the detector detects the radioactive emission directly without requiring any scintillation materials. In such embodiment, it is preferable to place the detector as close to the tube as possible. In such embodiment, however, the radioactive emission must be strong enough to penetrate the electrolyte buffer as well as the tube wall. Thus, such technique calls for the use of energetic radio-labels which may be more hazardous for handling and disposal. For this reason, it may be desirable to provide an alternative embodiment where less energetic radio-labels may be used instead. As noted above, the radioactive emission from such less energetic radio-labels may be incapable of penetrating the electrolyte or the tube wall.

FIG. 3 is a capillary electropherogram of quanosine 5'[$\alpha$-$^{32}P$] triphosphate (peak 1) and adenosine 5'[$\alpha$-$^{32}P$] triphosphate (peak 2), to illustrate the invention. The electropherogram of FIG. 3 is obtained using $^{32}P$ as radio-label and a CdTe detector described above in reference to FIGS. 1 and 2.

FIGS. 4A and 4B show a section of the capillary tube 12 equipped with scintillating material to aid the detection of such weak radio-labels. As shown in FIG. 4A, tube 12 contains scintillating beads 62 contained within frits 64 to keep the beads in place in the capillary and to prevent them from being dislodged by the movement of the electrolyte. The scintillating beads are placed adjacent to detector 22 in reference to FIG. 1. Thus when a component which has been radio-labeled passes through the section of tube 12 containing beads 62, the radioactive emission from the radio-label causes the beads to fluoresce. Such fluorescent light will penetrate tube 12 to be detected by detector 22. Since such light is able to travel to locations away from the tube 12, detector 22 may be placed at locations away from the tube.

FIG. 4B shows a section of tube 12 where a portion of the tube is made of a scintillating wall material 72.

Similar to the embodiment of FIG. 4A, the portion 72 is placed adjacent to detector 22 in reference to FIG. 1 for the detection of the weak radio-label in a similar manner as an embodiment of FIG. 4A.

FIG. 5 is a diagram of a portion tube 12 connected to a portion of a second tube 90 to permit a flowing stream of scintillating material to be introduced into tube 12 from the second tube 90. The scintillating material will then emit light in response to radiation from the radio-label on components of the sample. For a detailed description of the connection that can be made between the capillary tube and second tube 90, see U.S. patent application entitled "Capillary Device", Ser. No. 07/235,953, filed Aug. 24, 1988 by Richard N. Zare and Xiaohua Huang, which is incorporated herein by reference.

The embodiemnts described above in reference to FIGS. 4A, 4B, and 5 are advantageous since the scintillation material is introduced into the capillary tube or forms a part of the tube itself. Therefore, the radioactive emission from the radio-label need not penetrate the capillary tube in order to cause the scintillation material to emit light. Light from the scintillation material, on the other hand, can easily penetrate the transparent capillary tube to be optically detected by an optical detector outside the tube. For this reason, less energetic radioactive materials may be used to radio-label sample components. Therefore, such embodiments permit a wider selection of radioactive materials to be used than Altria et al.'s device. This versatility greatly extends the usefulness of capillary electrophoretic separation.

In conventional capillary electrophoretic systems, high voltages of the order of 20,000 or 30,000 volts are applied. Such high voltages are applied to increase the speed of movement of the electrolyte in the tube and to thus reduce the amount of time required for separating a sample into its components. In reference to FIG. 1, detector 22 detects the presence of components of a sample when such components actually pass the portion of tube 12 next to detector 22. The time interval during which a sample or a component of a sample spends in the vicinity of the detector is known as the residence time. When voltages on the order of 20,000 or 30,000 volts are applied, the residence times of the components of a sample are short, typically a few seconds. Such short residence times would limit the sensitivity of detection of the system. The control system 100 of FIG. 6 in conjunction with the programmable high voltage power supply 20, enable the sensitivity of detection to be improved compared to conventional systems with only slightly degraded speed performance of the system.

FIG. 6 is a block diagram of electrophoretic system 10 and a control system 100 for adjusting the voltage applied by power supply 20 of FIG. 1 to increase the sensitivity of detection to illustrate the preferred embodiment of the invention. As shown in FIG. 6, control system 100 includes a computer 102 and an interface 104. The electrophoretic system 10 is shown in more detail in FIG. 1. In one embodiment, detector 22 is of a type which generates pulses in response to the detection of radioactivity or light. Interface 104 counts the number of pulses received from detector 22 and supplies the number of pulses counted over a pre-selected time interval to computer 102. In the preferred embodiment, interface 104 may simply be a counter with a digital output. In such embodiment, the counter is simply reset to zero at the expiration of the time period, at which point the counter starts counting for the next preselected time period.

Detector 22 provides pulses in response to background noise such as electronic noise, ambient radioactivity or light. The threshold value set in the computer is higher than the digital output of the counter caused by background noise. Preferably the threshold value in computer 102 is set several times that of the count corresponding to background noise to prevent undesired triggering of the control system 100.

When the sample is first injected into tube 12, a high voltage is applied to the tube since it is desirable to move electrolyte through the tube at a relatively high speed until the components reach the detector 22. Therefore, upon injection of the sample into tube 12, a high voltage is applied to tube 12 as described above in reference to FIG. 1. While the electrolyte and the sample are moved through the tube, detector 22 provides pulses to interface 104, and interface 104 in turn counts the pulses and provides an output count to computer 102. Computer 102 compares the count from interface 104 to the threshold value. When such count is below the threshold, this indicates that detector 22 has not detected any components of the sample. In such event, computer 102 takes no action and a high voltage continues to be applied to tube 12 so that the electrolyte buffer containing the sample would continue to flow through tube 12 at a relatively high speed. When computer 102 determines that the count from interface 104 exceeds the set threshold value, this indicates that the detector 22 has detected a component of the sample; in such event, computer 102 causes power supply 20 to supply a lower voltage to tube 12, thereby slowing down the flow of the sample and the electrolyte buffer through tube 12. This will result in an increase in the residence time of the particular component which is passing detector 22, thereby increasing the sensitivity of detection. Once the labelled sample component has passed through the detection volume, the count rate sensed by detector 22 and computer 102 will fall below the threshold value and computer 102 will cause power supply 20 to return to the original higher voltage until such time as the threshold is again exceeded by additional radio-labelled samples. In this manner, the residence time of each sample component is increased without unnecessarily lengthening the overall analysis time. If desired, computer 102 can cause power supply 20 to be turned off, so that the particular component detected will stay in the vicinity of detector 22 and can be detected or measured for a longer time period, where such time period is limited only by the time during which the already separated components of the sample will remain separated and not become mixed as a result of diffusion.

After a component of a sample has passed the detector, it is possible to bring the component back to the detector using the control system 100 in cooperation with system 10. When computer 102 detects that the count from interface 104 exceeds the threshold value, indicating the presence of a component of the sample, and that subsequently the count falls to a value below the threshold value, computer 102 will supply a signal to power supply 20, causing power supply 20 to supply a voltage of opposite polarity to tube 12, thereby causing the electrolyte buffer together with the sample to move in a direction opposite to that in which the electrolyte was moving previously. This has the effect of causing the component of the sample which has passed the detector for a first time to reverse direction and pass the detector a second time. The voltage of opposite polarity applied by power supply 20 can be selected so that the residence time of the component of such sample will be of a desired value to increase the sensitivity of detection during the second pass. During the second pass, when computer 102 detects that the count from interface 104 again exceeds the threshold value and subsequently falls to below such threshold value, computer 102 can cause power supply 20 to again revert polarity so that a component of the sample will pass the detector a third time. In such manner the component of the sample can be detected for three or more times.

Where the component is made to pass the detector for more than one time, the signals from the detector during the two or more passes may be cross-correlated to increase the signal to noise ratio. Thus detector 22 provides a digital signal train corresponding to the amplitude variation of the radiation received by the detector during a pass by the component. To increase the signal to noise ratio, such signal is correlated with other digital signal trains from the detector during other passes. Such cross-correlation techniques are described, for example, in:

1. "Gas Chromatographic Studies of Rapid Repeated Injections of Samples into a Column", Donald Macnaughtan, Jr. and L. B. Rogers, *Analytical Chemistry*, Vol. 43, No. 7, pp. 822-827, June 1971.

2. "Continuous Chromatographic Analysis Using a Pseudo Random Sample Switching Function", Raymond Annino and L. E. Bullock, *Analytical Chemistry*, Vol. 45, No. 7, pp. 1221-1227, June 1973.

3. "Random Input and Correlation Methods to Improve the Signal-to-Noise Ratio in Chromatographic Trace Analysis", H. C. Smit, *Chromatographia* 3, pp. 515-519, 1970.

4. "Gas Chromatographic Response as a Function of Sample Input Profile", Charles N. Reilley, Gary P. Hildebrand and J. W. Ashley, Jr., *Analytical Chemistry*, pp. 1198-1213.

5. "Cross-Correlation Chromatography Applied to Gas-Solid Adsorption Studies", J. B. Phillips and M. F. Burke, *Journal of Chromatographic Science*, Vol. 14, pp. 495-497, October 1976.

6. "Multiplex Gas Chromatography", John B. Phillips, *Analytical Chemistry*, Vol. 52, No. 4, pp. 468A-474A, April 1980.

7. "Fluidic Logic Element Sample Switch for Correlation Chromatography", Raymond Annino, Marie-France Gonnord and Georges Gulochon, *Analytical Chemistry*, Vol. 51, No. 3, pp. 379-382, March 1979.

The feature described above in reference to FIG. 6 increases sensitivity of detection. Such feature is applicable not only to processes using radio-labels but to any capillary electrophoretic process. All such applications are within the scope of the invention. The above description of the details of implementation, method and composition are merely illustrative of the invention. Different variations may be within the scope of the invention which is to be limited only by the appended claims

We claim:

1. An electrophoretic apparatus for detecting the presence of a component in a sample introduced into a capillary tube, said apparatus comprising:
    means for applying a voltage to the capillary tube to move the sample in the tube for separating the sample into its components;
    a detector placed in or near the tube for detecting a characteristic of a component of the sample, said detector providing signal when said component is detected; and
    feedback means responsive to the signal for adjusting the voltage applied by the voltage applying means so as to adjust the speed of movement of the sample in the tube to increase sensitivity of detection.

2. The apparatus of claim 1, wherein said feedback means causes no voltage to be applied to the tue in response to the signal, thereby causing the movement of the sample in the tube to be stopped in order to increase the time spent by the component near the detector.

3. The apparatus of claim 1, wherein said feedback means reverses the direction of the voltage applied in response to the signal after the component has passed the detector, thereby causing the movement of the sample in the tube to be reversed in direction in order to cause the component to pass the detector by one additional time.

4. The apparatus of claim 3, further comprising signal processing means for correlating the signals from the detector corresponding to the two or more passages of the component by the detector to increase signal to noise ratio.

5. The apparatus of claim 1, wherein said feedback means causes the voltage applying means to reduce the voltage applied to the tube, thereby reducing the speed of the movement of the sample in the tube in order to increase the time required by the component to pass the detector.

6. The apparatus of claim 1, said detector detecting the presence of the component by detecting physical properties of the component.

7. The apparatus of claim 6, said component emitting radiation, said detector detecting the physical properties of the component by detecting radiation from the component.

8. The apparatus of claim 1, said signal provided by the detector having an amplitude varying directly with the amount of the component detected by the detector; and
    wherein said feedback means compares the amplitude of the signal to a predetermined threshold and adjusts the voltage applied by the voltage applying means to the capillary tube when the amplitude of the signal exceeds the threshold, thereby adjusting the speed of movement of the sample in the tube and increasing sensitivity of detection.

9. The apparatus of claim 8, wherein said feedback means causes the voltage applying means to apply no voltage to the tube when the amplitude of the signal exceeds the threshold, thereby causing the movement of the sample 10. The apparatus of claim 8, wherein said feedback means causes the voltage applying means to reduce the voltage applied to the tube when the amplitude of the signal exceeds the threshold, thereby reducing the speed of the movement of the sample in the tube in order to increase the time required by the component to pass the detector.

11. The apparatus of claim 8, wherein said feedback means causes the voltage applying means to reverse the direction of the voltage applied to the capillary tube when the amplitude of the signal falls to a value below the threshold after exceeding the threshold, thereby causing the movement of the sample in the tube to be reversed in direction in order to cause the component to pass the detector for at least one additional time.

12. An electrophoretic method for detecting the presence of a component in a sample introduced into a capillary tube by means of a detector in or near the tube, said method comprising:
   applying a voltage to the capillary tube to move the sample in the tube for separating the sample into its components;
   detecting by means of said detector a characteristic of a component of the sample and providing a signal when said component is detected; and
   adjusting the voltage applied in the voltage applying step in response to the signal in a feedback action to adjust the speed of movement of the sample in the tube to increase sensitivity of detection.

13. The method of claim 12, said signal provided in the detecting and providing step having an amplitude varying directly with the amount of the component detected by the detector; and
   wherein said adjusting step includes comparing the amplitude of the signal to a predetermined threshold and adjusting the voltage applied in the voltage applying step when the amplitude of the signal exceeds the threshold to adjust the speed of movement of the component in the tube and to increase sensitivity of detection.

14. The method of claim 13, wherein said adjusting step reverses the direction of the voltage applied to the capillary tube when the amplitude of the signal falls to a value below the threshold after exceeding the threshold, thereby causing the movement of the sample in the tube to be reversed in direction in order to cause the component to pass the detector for at least one additional time.

15. The method of claim 14, further comprising correlating the signals from the detector corresponding to the two or more passages of the component detected by the detector to increase signal to noise ratio.

16. The method of claim 12, wherein said adjusting step comprises reducing the voltage applied to the capillary tube to decrease the speed of movement of the component past the detector.

17. The method of claim 12, wherein said adjusting step comprises stopping the application of voltage to the capillary tube, thereby causing the movement of the component in the tube to be stopped in order to increase the time spent by the component near the detector.

18. An electrophoretic apparatus for detecting the presence of a component in a sample, said apparatus comprising:
   a capillary tube for holding a sample introduced therein, said tube defining a separation zone therein for separation of the sample into its components;
   means for applying a voltage to the capillary tube to move the sample in the tube, for separating the sample into its components in the separation zone;
   a detector placed in or near the separation zone of the tube for detecting a characteristic of a component of the sample, wherein the separation zone in the tube has substantially the same cross-sectional dimensions, said detector providing a signal when said component is detected; and
   feedback means responsive to the signal for adjusting the voltage applied by the voltage applying means so as to adjust the speed of movement of the sample in the tube to increase sensitivity of detection.

19. The apparatus of claim 18, wherein the tube has as inlet and has an outlet downstream in the path of the sample from the detector, and wherein the inside cross-sectional dimensions of the tube are substantially the same between the inlet and the outlet.

* * * * *

UNITED STATES PATENT AND TRADEMARK OFFICE
CERTIFICATE OF CORRECTION

PATENT NO. : 5,232,565

DATED : August 3, 1993

INVENTOR(S) : Zare et al.

It is certified that error appears in the above-indentified patent and that said Letters Patent is hereby corrected as shown below:

| Item | |
|---|---|
| [75] on Cover Page | Delete listing of inventors and replace with: --Richard N. Zare, Stanford, Calif.; Stephen L. Pentoney, Jr., Menlo Park, Calif.-- |
| [73] on Cover Page | Replace "Standford" with --Stanford-- |
| Column 8, Line 3, in Claim 1 | Replace "providing signal" with --providing a signal" |
| Column 8, Line 11, in Claim 2 | Replace "tue" with --tube-- |
| Column 8, Line 55, in Claim 9 | Replace "the sample" with --the sample in the tube to be stopped in order to increase the time spent by the component near the detector.-- |

UNITED STATES PATENT AND TRADEMARK OFFICE
CERTIFICATE OF CORRECTION

PATENT NO. : 5,232,565

DATED : August 3, 1993

INVENTOR(S) : Zare, et al

It is certified that error appears in the above-indentified patent and that said Letters Patent is hereby corrected as shown below:

Column 10, line 32, claim 19, replace "as" with --an --.

Signed and Sealed this

Fourteenth Day of June, 1994

Attest:

BRUCE LEHMAN

Attesting Officer

Commissioner of Patents and Trademarks